(12) United States Patent
Buhr et al.

(10) Patent No.: US 8,246,931 B1
(45) Date of Patent: Aug. 21, 2012

(54) DEVELOPMENT OF A QUAIL EMBRYO MODEL FOR THE DETECTION OF BOTULINUM TOXIN

(75) Inventors: Richard J. Buhr, Athens, GA (US); Dianna V. Bourassa, Monroe, GA (US); Larry J. Richardson, Hull, GA (US); Lynda C. Kelley, Watkinsville, GA (US); Nelson A. Cox, Jr., Athens, GA (US); Robert W. Phillips, Watkinsville, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 201 days.

(21) Appl. No.: 12/508,380

(22) Filed: Jul. 23, 2009

Related U.S. Application Data

(60) Provisional application No. 61/082,972, filed on Jul. 23, 2008.

(51) Int. Cl.
*A61K 49/00* (2006.01)

(52) U.S. Cl. ....... 424/9.1; 424/9.2; 424/236.1; 424/581; 424/582; 424/93.7; 424/247.1; 435/326

(58) Field of Classification Search .................. None
See application file for complete search history.

(56) References Cited

U.S. PATENT DOCUMENTS 8,137,924 B2 * 3/2012 Chapman et al. ............ 435/7.32

* cited by examiner

*Primary Examiner* — Jennifer Graser
(74) *Attorney, Agent, or Firm* — Gail E. Poulos; Leslie Shaw; John D. Fado

(57) ABSTRACT

A method for using bird eggs to detect the presence of at least one botulinum toxin.

4 Claims, 14 Drawing Sheets

DEVELOPMENT OF A QUAIL EMBRYO MODEL FOR THE DETECTION OF BOTULINUM TOXIN

REFERENCE TO RELATED APPLICATION

This application claims the benefit of U.S. Provisional Application No. 61/082,972, filed 23 Jul. 2008, which is incorporated herein by reference in its entirety.

BACKGROUND OF THE INVENTION

1. Field of the Invention

This invention relates to a method for the detection of botulinum toxin using bird eggs.

2. Description of the Related Art

Botulinum neurotoxins (BoNTs) produced by *Clostridium botulinum* block the release of acetylcholine from motor and autonomic nerve termini which leads to flaccid paralysis of afflicted muscles. In mammals paralysis of the diaphragm and intercostal muscles results in ventilatory failure and hypoxia which progresses to brain failure and death. In humans, botulism is primarily caused by ingestion of strains of *C. botulinum* that produce toxin serotypes A, B, and E and rarely C and F.

The medicinal use of purified type A botulinum toxin (BoNT/A) is expanding at a rapid rate to treat muscle anomalies where hyperactivity results in sustained contractions causing twisted or abnormal posture (strabismus, blepharospasm, torticollis, or achalasia) or where hyperexcitability results in muscle twitching (cervical dystonia, oromandibular dystonia, or spasmodic dystonia) which can be reduced or relieved by muscle paralysis. In addition, BoNT/A is utilized in commercial application for cosmetic uses for the disappearance of frown lines, diminishing facial wrinkles, or intradermal injection to reduce axillary hyperhidrosis. At least ten fold of the medicinal treatment dose would be required to enter the circulatory system to manifest systemic symptoms of botulism in humans (approximately 0.09-0.15 µg intravenously or intramuscularly for a 70-kg human, or a calculated corresponding 70-90 µg oral dose has been extrapolated from trials in primates).

The unintentional ingestion of BoNT in foods has been a health issue for centuries and while botulism in humans is rare it remains a potentially fatal illness. There are typically fewer than 30 cases of foodborne botulism reported annually in the United States. BoNT has also been evaluated as an agent in biological weaponry and is considered the most potent lethal natural toxin known The initial neurological symptoms of ingested BoNT in humans are ptosis, blurred vision and diplopia followed by dysphonia, dysarthria, and dysphagia. Peripheral muscle weakness consists of descending paralysis affecting first the cranial nerves, then the arms, respiratory muscles, to the legs with onsets from 18 to 36 h after exposure by ingestion. In severe cases, extensive respiratory muscle paralysis leads to ventilatory failure progressing to death unless ventilatory support is provided (<72 h for mice and within 1 to 150 days for humans from the time that symptoms were first detected).

Currently, the mouse toxicity and neutralization bioassay (mouse $LD_{50}$) is used to analyze samples for the presence of BoNT types A to G activity. In the 16-24 g mouse as little as 10 pg of BoNT/A injected intraperitoneal can be detected within 6 to 96 h. BoNT/A has an $LD_{50}$ in mice of 1 ng/kg (1 mouse Unit=0.02-0.03 ng BoNT) and is detectable within 72 h. The mouse bioassay is a functionality assay that can detect all 7 biologically active BoNT/A to G. The assay requires a three part approach: toxin screening, toxin titer determination, and finally toxin neutralization using monovalent antibodies for each serotype. This process typically requires 6 days, 2 days of analysis at each part. The potency dosage determination for medicinal BoNT/A with the mouse assay typically utilizes at least 48 mice per test with an additional 48 for the reference sample.[14] There is growing pressure to replace the mouse $LD_{50}$ assay for ethical concerns over the use of death by asphyxiation of the mice as the test endpoint. There are also scientific concerns over the continued use of a variable animal bioassay for medicinal potency dosage determination when equally as sensitive alternative methods have been reported for simple matrices that may achieve refinement, reduction, and replacement of the use of mice for botulinum toxin texting.

Institutional Animal Care and Use Committee guidelines recommend that animals are to be preemptively euthanized upon observing the earliest onset of severe signs of distress; because severe pain, suffering, or death of experimental animals should be avoided as routine experimental endpoints. $LD_{50}$ tests are controversial due to the ethics of using a large number of animals and evaluating mainly mortality. Toxicity $LD_{50}$ testing procedures should incorporate the principles of reduction and refinement until alternative test methods are validated. Preemptive euthanasia of animals should be standard protocol upon exhibiting the progressive signs of a predictable death, an impending death, or when entering into a moribund state. The endpoint for the mouse $LD_{50}$ assay is commonly death by asphyxiation. In the mouse $LD_{50}$ assay, when the injected dose is high (as for medicinal potency determination), mice typically develop signs of botulism and death ensues within 8 h. At lower doses, mice are afflicted more slowly; therefore requiring observation every 2 h over the 4 days before negative results are observed and recorded for the assay. The onset of morbidity requires increased frequency of observations, isolation of individual morbid animals, and the removal of dead animals as promptly as possible. The mouse model also inherently has potential safety concerns in that the mice may move during injection leading to the possibility that the researchers could accidentally inject themselves instead of the mouse. Therefore, laboratory personnel who work with BoNTs at unknown dosages on a routine basis and/or inject mice are encouraged to be vaccinated with the botulinum toxoid vaccine. Mice colonies are also expensive to maintain and require daily care and observation. Therefore, complementary models to the mouse would be highly valued.

Currently the mouse assay is used as the model for assessment of botulinum toxin activity. However, the mouse model poses some problems such as the time length needed for the assay (up to 36 hours) as well as safety concerns and requirements for handling needles and live animals which could cause the handler to accidentally self-inject the toxin. While various methods have been developed for the detection of botulinum toxin there remains a need in the art for a quicker method that overcomes the safety issues of the current mouse assay. The present invention's new botulinum toxin detection method of incubating quail embryos overcomes the limitations of the prior art.

SUMMARY OF THE INVENTION

It is therefore an object of the present invention is to provide a method for detecting at least one botulinum toxins using in ovo avian embryos.

A further object of the present invention is to provide an system for detecting botulinum toxin wherein said system includes an automated means for introducing botulinum toxin in ovo to avian embryo.

Further objects and advantages of the invention will become apparent from the following description.

BRIEF DESCRIPTION OF THE DRAWINGS

FIG. 1 shows embryo viability after eggs were injected with 100 µL of saline, 10, 100, 150, 200, or 250 ng/egg botulinum toxin type A dosages using a 29 gauge, half inch needle and 1.0 mL tuberculin syringe. Following injection, eggs were placed vertically back onto egg flats and incubated at 37.2 C without further turning. Pans of water were placed in the incubator to increase relative humidity to approximately 70%. After 1, 2, and 3 days following injection the viability of each embryo was assessed by both candling and motion detection. FIG. 1A shows the numbers of embryos alive while FIG. 2 shows embryo viability after eggs were injected with 100 µL of saline, 5, 10, 20, 30, 40 or 50 ng/egg botulinum toxin type A dosages using a 29 gauge, half inch needle and 1.0 mL tuberculin syringe. Following injection, eggs were placed vertically back onto egg flats and incubated at 37.2 C without further turning. Pans of water were placed in the incubator to increase relative humidity to approximately 70%. After 1, 2, and 3 days following injection the viability of each embryo was assessed by both candling and motion detection. FIG. 2A shows the numbers of embryos alive while FIG. 3 shows embryo viability after eggs were injected with 100 µl, of saline, 1, 5, 10, 20, 30, 40 or 50 ng/egg botulinum toxin type A dosages using a 29 gauge, half inch needle and 1.0 mL tuberculin syringe. Following injection, eggs were placed vertically back onto egg flats and incubated at 37.2 C without further turning. Pans of water were placed in the incubator to increase relative humidity to approximately 70%. After 1, 2, and 3 days following injection the viability of each embryo was assessed by both candling and motion detection. FIG. 3A shows the numbers of embryos alive while

FIG. 6 shows a compilation of the data shown in FIGS. 4 and 5.

FIG. 7 shows the final state of embryonic development for nonviable embryos, as determined by degree of yolk sac retraction into the abdominal cavity, expressed as a percentage of the total number of nonviable embryos for each toxin dosage group. Yolk sac retraction stages: Stage 44=yolk sac not initiated retraction, stage 45=yolk sac ½ retracted, state 45+=yolk sac ¾ retracted, and state 46=yolk sac fully retracted.

FIG. 8 shows the final state of embryonic development, as determined by stage of pipping, expressed as a percentage of the total number of nonviable embryos for each toxin dosage group. Stages of pipping: not pipped into the aircell, pipped into the aircell, or pipped through the eggshell.

FIG. 9 shows the viability of the UGA C-line embryos injected with the gelatin phosphate buffer with 0 ng of toxin was 90% at 3 days post-injection. Embryos injected with BoNT/A at dosages from 1, 5, 10, 20, to 40 ng had consistently low viability for all dosages at 10, 20, 25, 10, and 30%. Those embryos injected with BoNT/F at dosages of 1, 5, 10, 20, to 40 ng had progressively lower viability with increasing dosages from 80, 50, 30, 40, to 10% viable.

FIG. 10 shows that embryos injected with trypsin activation solution with 0 ng of toxin resulted in 80% viable embryos indicating a slight depression in viability attributable to trypsin. Embryos injected with trypsin activated BoNT/B at 10, 20, 40, 80 ng had viability of 60, 0, 0, and 0% and those injected with trypsin activated BoNT/E had viabilities of 10, 20, 0, and 0%.

DETAILED DESCRIPTION OF THE INVENTION

Figure 1A:
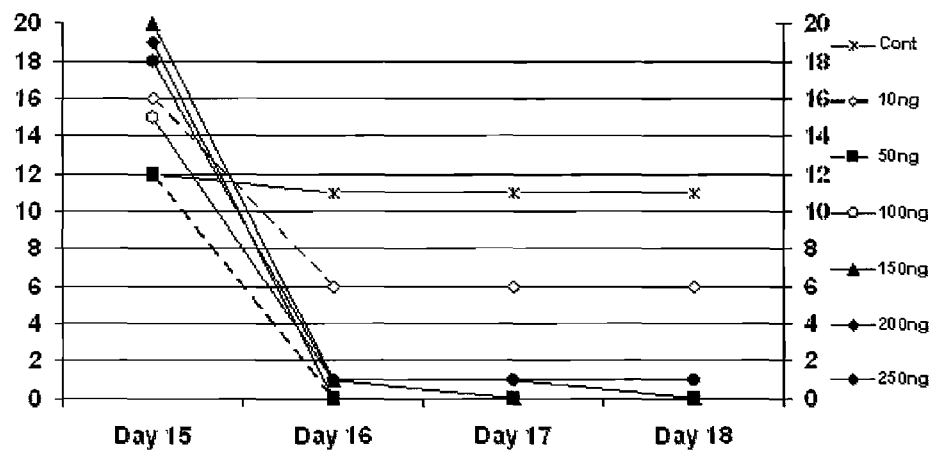

*Clostridium botulinum* is a ubiquitous microorganism which under anaerobic conditions can produce botulinum toxins. Due to both food-borne illness and the potential use of botulinum toxin as a biological weapon, the ability to assess the amount of toxin in a food or environmental sample is important.

For an alternative bioassay, Japanese quail embryos/eggs were chosen for their relatively small egg size of approximately 10-12 g (compared to other domestic poultry species). The small size is preferred due to the relatively lower amounts of toxin that would be required and the shorter total incubation period of quail, about 18 days. Injection of quail embryos with Botulinum toxin Type A at day-15 of incubation (prior to pipping into the air cell and initiation of pulmonary ventilation) should enable toxin activity detection by the failure of the embryo to progress and initiate internal pipping into the aircell and subsequent respiration ventilatory movements on approximately day-16 of incubation. Depending on the specific incubation and egg storage conditions, Japanese quail embryos typically pip into the aircell on about Day-15.5 of incubation and initiate the transition from aquatic (chorioallantoic membrane) to terrestrial (lungs) gas exchange for respiration. Pipping into the aircell enables the transition to pulmonary respiration and thoracic ventilatory movements prior to eggshell pipping on about Day-16, and the completion of hatching on about Day-18 of incubation.

The invention is practiced with embryos in ovo, particular bird or avian eggs, and more particularly poultry eggs, such as quail chicken, turkey, duck, geese, pheasant or ostrich eggs. The eggs need to be viable eggs. These embryos, between about 14-15 days of incubation, are then injected with botulinum toxin through the eggshell membrane and into the neck. The injection was carried out using a means for delivery of a liquid composition, in this instance of the invention, a needle was used. Following injection, the eggs need to be oriented vertically, and labeled for the type of injection received. At about 1, 2, and 3 days post-injection the viability of each embryo is reassessed by both candling and motion detection. The motion detection being accomplished with a digital egg monitor using an infrared light beam and detects embryo motion by the change in the light pattern, as early as, about 7 days of incubation for quail embryos. The monitor then counts the pulses and calculates heart beats per minute. If the embryo pips into the aircell or through the eggshell then heart rate is no longer able to be calculated and rectangular waves are displayed. This is the pattern for the control groups. If the embryo is paralyzed, pulse rate is not able to be detected and a flat line is displayed on the monitor. If three consecutive flat lines are recorded than the embryo is then considered nonviable.

At the end of about day 18 of incubation, all unhatched eggs are opened and the embryos examined and classified by stage of embryonic development, as modified for type of avian embryo used, by observing the degree of yolk sac retraction, and if the embryo had piped into the aircell or through the eggshell.

For the purposes of this invention the term plurality of eggs shall be defined as a group comprising of at least two eggs sufficient to generate a statistically significant result.

It is envisioned that a high speed automated injection system for avian embryos will be particularly suitable for practicing the present invention. Numerous such devices are available, exemplary being those disclosed in U.S. Pat. Nos. 4,040,388, 4,469,047 and 4,593,646, all to Miller, the disclosures of which are incorporated herein by reference. All such devices, as adapted for practicing the present invention, comprise an injector, the injector containing an injection liquid, the injection liquid containing a bacterial culture as described herein, with the injector positioned to inject an egg carried by the apparatus with the bacterial culture. Other features of the apparatus are discussed above. In addition, if desired, a sealing apparatus connected to the supporting frame and operatively associated with the injection apparatus may be provided for sealing the hole in the egg after injection thereof with a suitable sealing material.

The following examples are intended only to further illustrate the invention and are not intended to limit the scope of the invention as defined by the claims.

EXAMPLE 1

Quail eggs were collected for 2 days from the random bred control line "C" of Japanese quail (*Coturnix japonica*) maintained at the University of Georgia and held in an egg cooler at approximately 20° C. until setting for incubation at weekly intervals. Eggs were incubated at approximately 37.7° C. with approximately 55% relative humidity and automatically turned through a 90° arc every hour. On day 14 of incubation, embryo viability was assessed by both light candling and motion detection (Digital Egg Monitor—Buddy V2, Avian Biotech International, Tallahassee, Fla., USA). Using the light candler, eggs containing viable embryos, the apex of the aircell was located and marked. The apex in the aircell margin indicates the neck/shoulder region of the embryo prior to pipping into the aircell, the site selected for toxin injection. At approximately 5-mm below the margin of the aircell a 2-mm diameter hole was then ground through the eggshell while leaving the shell membranes intact. A second 2-mm hole was ground at the top of the eggshell above the center of the aircell to permit rapid equalization of internal egg fluid pressure and minimize fluid backflow out of the embryo/egg immediately following injection. Eggs were placed into groups of 10 to 20 viable embryos on egg flats and returned to the hatcher-incubator operating at approximately 37.7° C. with the relative humidity raised to approximately 70%, to compensate for the increased water vapor conductance from the egg following grinding holes into the eggshell.

Figure 1B:
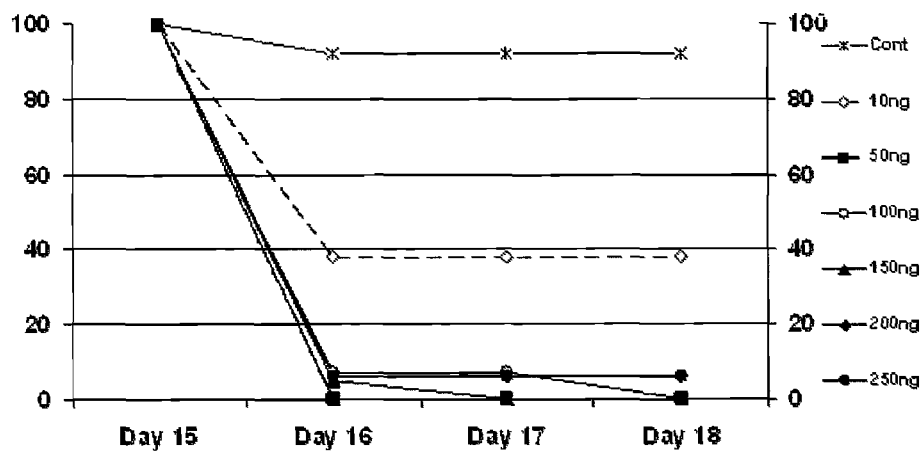
FIG. 1B shows the percentage of embryos alive
Figure 2A:
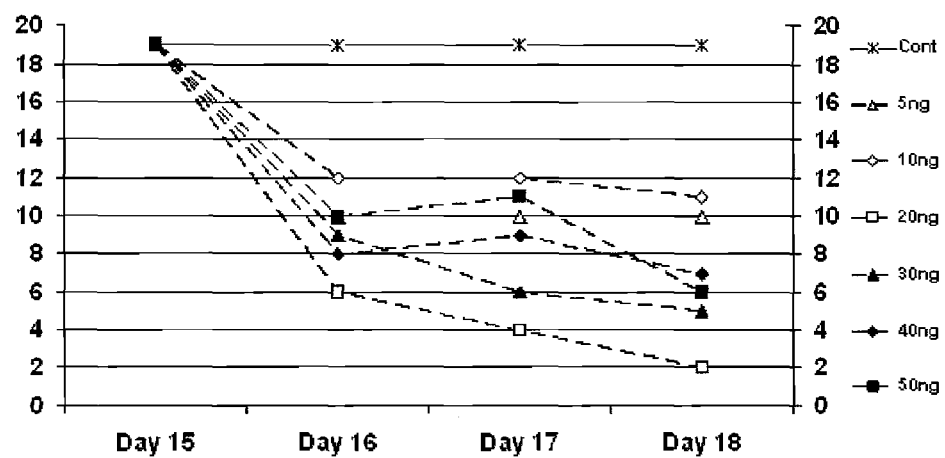
Figure 2B:
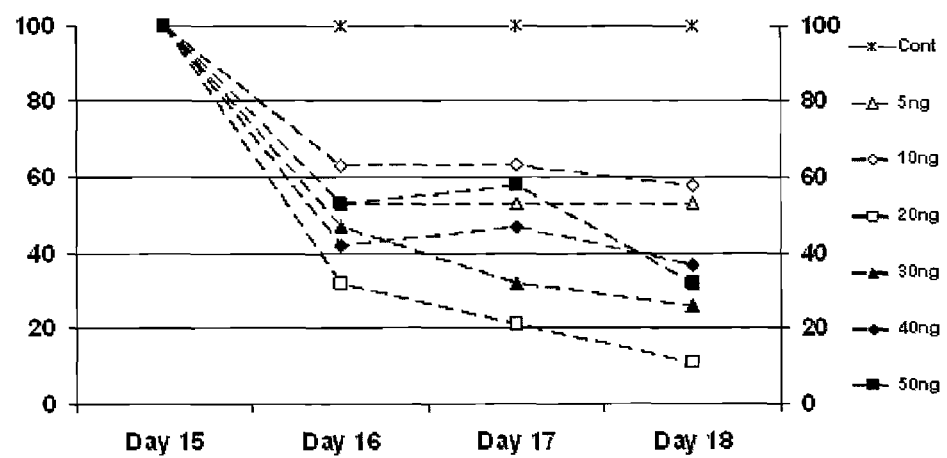
FIG. 2B shows the percentage of embryos alive
Figure 3A:
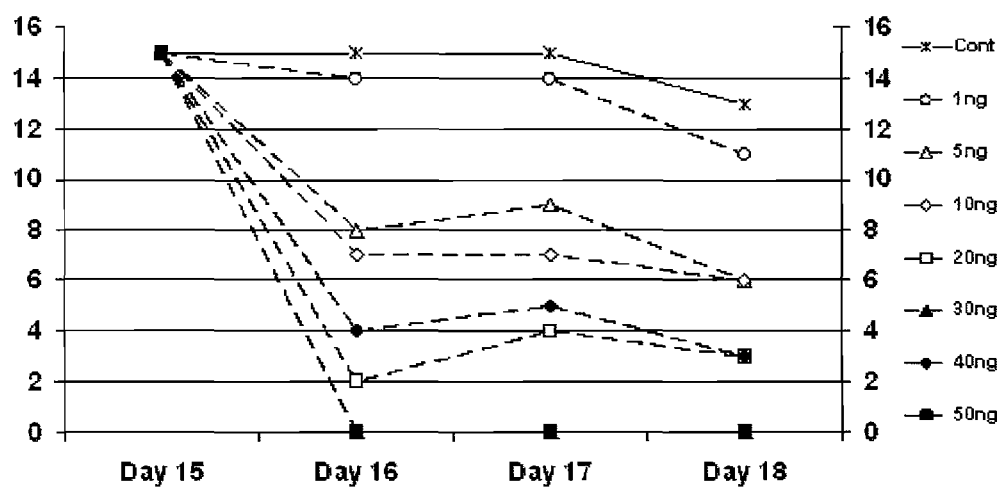
Figure 3B:
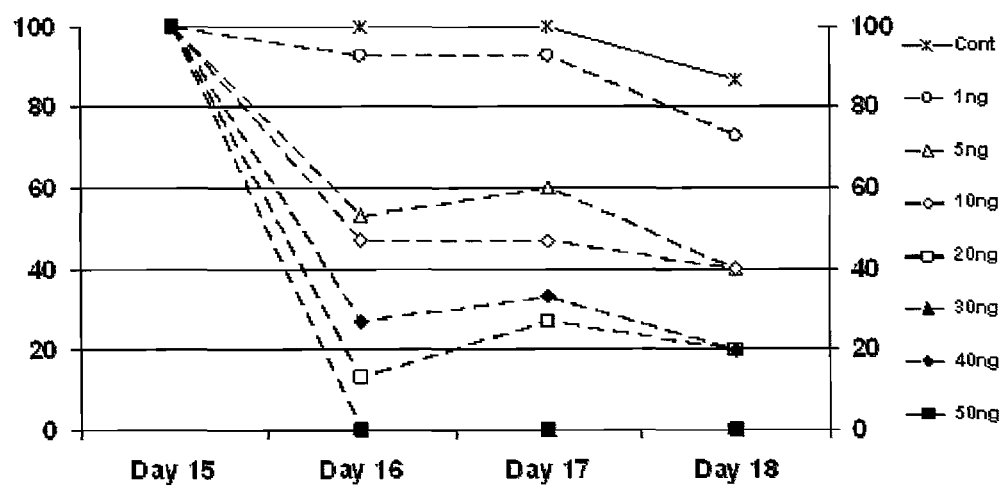
FIG. 3B shows the percentage of embryos alive
Figure 4A:
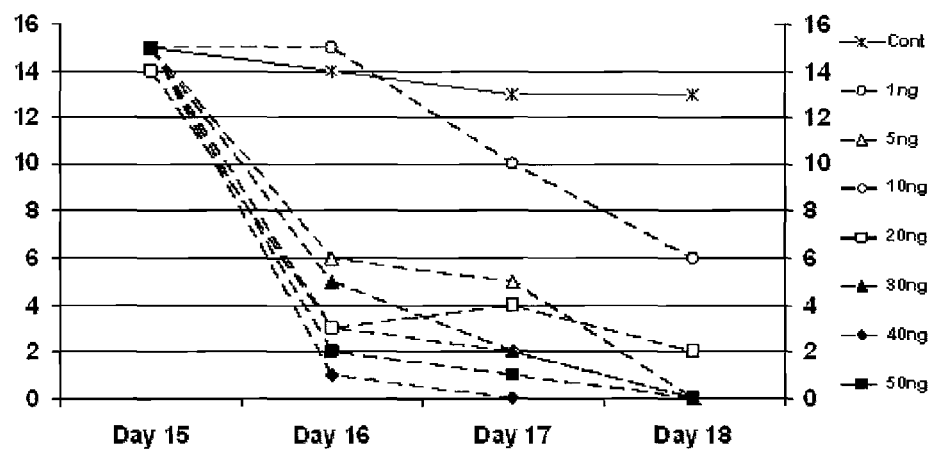
FIGS. 4A and 4B show embryo viability after eggs were injected with 100 µL of saline, 1, 5, 10, 20, 30, 40 or 50 ng/egg botulinum toxin type A dosages using a 29 gauge, half inch needle and 1.0 mL tuberculin syringe. Following injection, eggs were placed vertically back onto egg flats and incubated at 37.2 C without further turning. Pans of water were placed in the incubator to increase relative humidity to approximately 70%. After 1, 2, and 3 days following injection the viability of each embryo was assessed by both candling and motion detection.
Figure 4B:
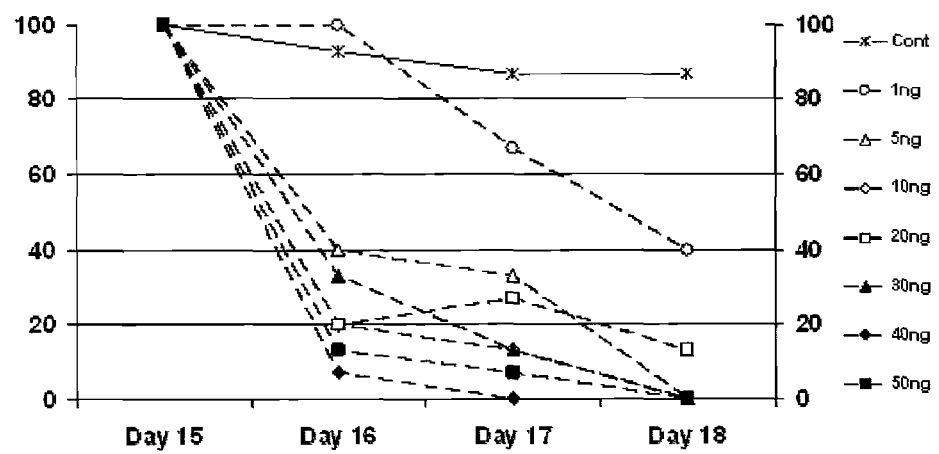
Figure 4C:
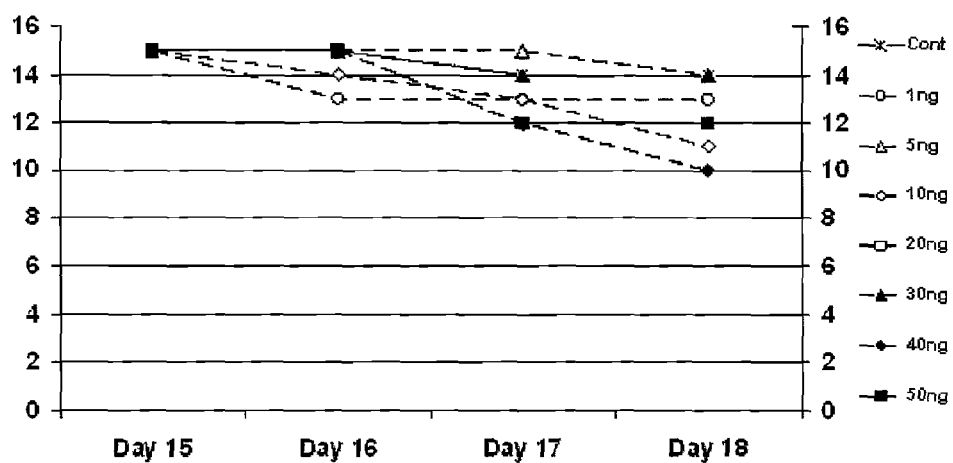
FIGS. 4C and 4D show embryo viability after eggs were injected with 100 µL of saline, 1, 5, 10, 20, 30, 40 or 50 ng/egg botulinum toxin type A dosages and an antitoxin antibody (for type A toxin, 10 µl, antibody added to 1.1 mL of toxin) and swirled for one hour prior to injection using a 29 gauge, half inch needle and 1.0 mL tuberculin syringe. Following injection, eggs were placed vertically back onto egg flats and incubated at 37.2 C without further turning. Pans of water were placed in the incubator to increase relative humidity to approximately 70%. After 1, 2, and 3 days following injection the viability of each embryo was assessed by both candling and motion detection.
Figure 4D:
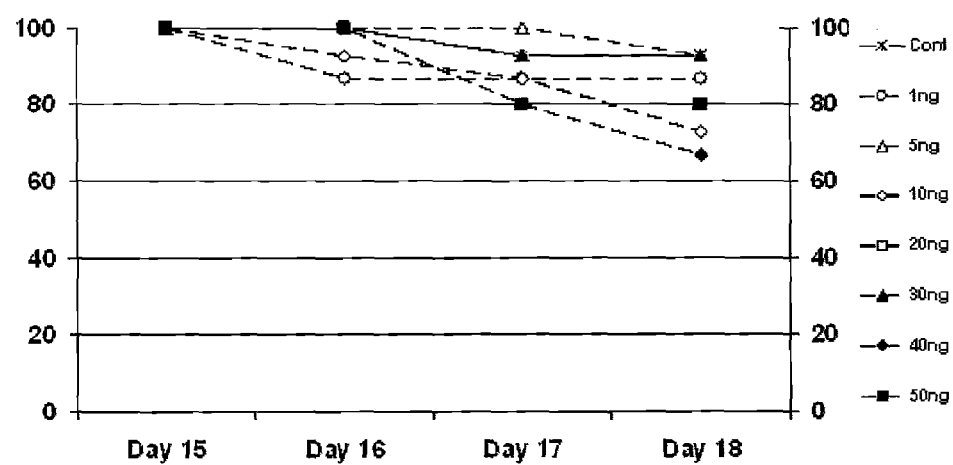
Figure 5A:
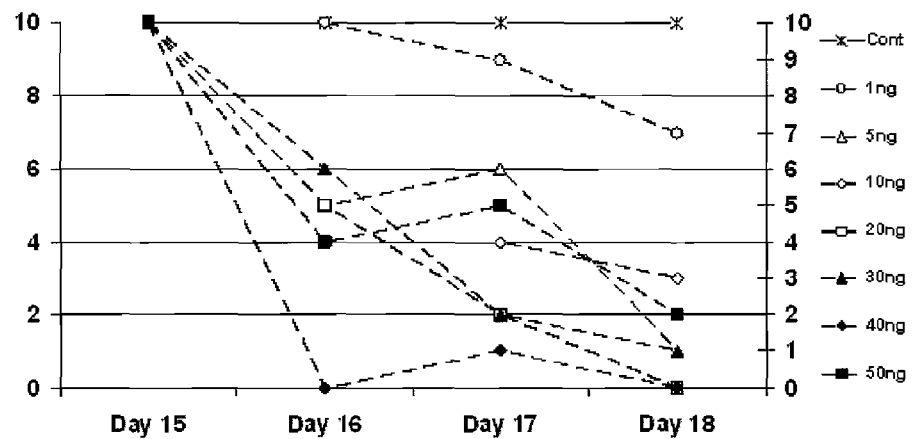
FIGS. 5A and 5B show embryo viability after eggs were injected with 100 µL of saline, 1, 5, 10, 20, 30, 40 or 50 ng/egg botulinum toxin type A dosages using a 29 gauge, half inch needle and 1.0 mL tuberculin syringe. Following injection, eggs were placed vertically back onto egg flats and incubated at 37.2 C without further turning. Pans of water were placed in the incubator to increase relative humidity to approximately 70%. After 1, 2, and 3 days following injection the viability of each embryo was assessed by both candling and motion detection.
Figure 5B:
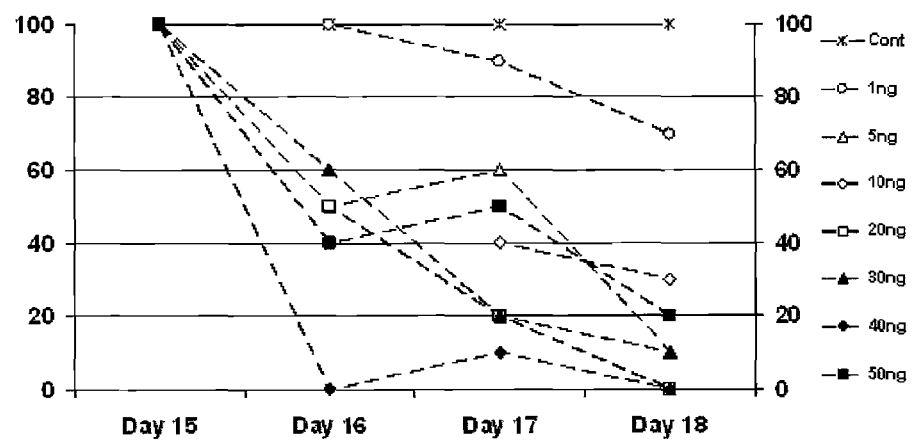
Figure 5C:
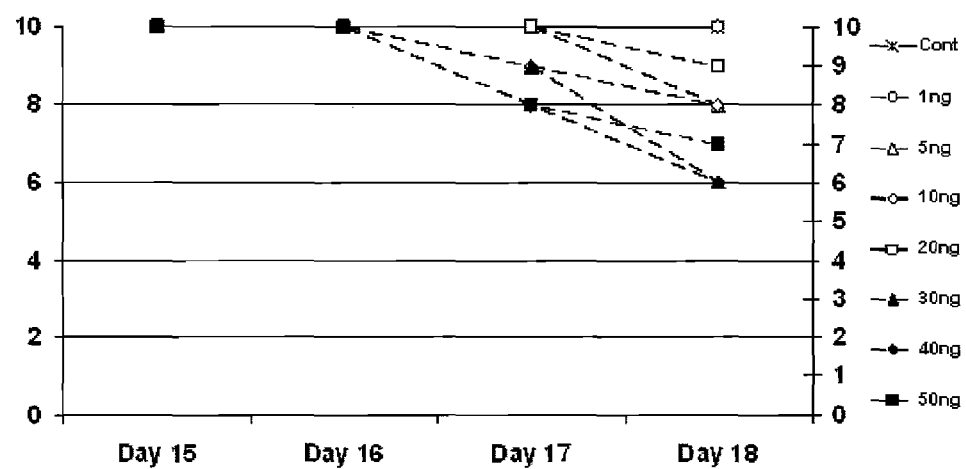
FIGS. 5C and 5D shows embryo viability after eggs were injected with 100 µL of saline, 1, 5, 10, 20, 30, 40 or 50 ng/egg botulinum toxin type A dosages and an antitoxin antibody (for type A toxin, 10 µL at antibody added to 1.1 mL of toxin) and swirled for one hour prior to injection using a 29 gauge, half inch needle and 1.0 mL tuberculin syringe. Following injection, eggs were placed vertically back onto egg flats and incubated at 37.2 C without further turning. Pans of water were placed in the incubator to increase relative humidity to approximately 70%. After 1, 2, and 3 days following injection the viability of each embryo was assessed by both candling and motion detection.
Figure 5D:
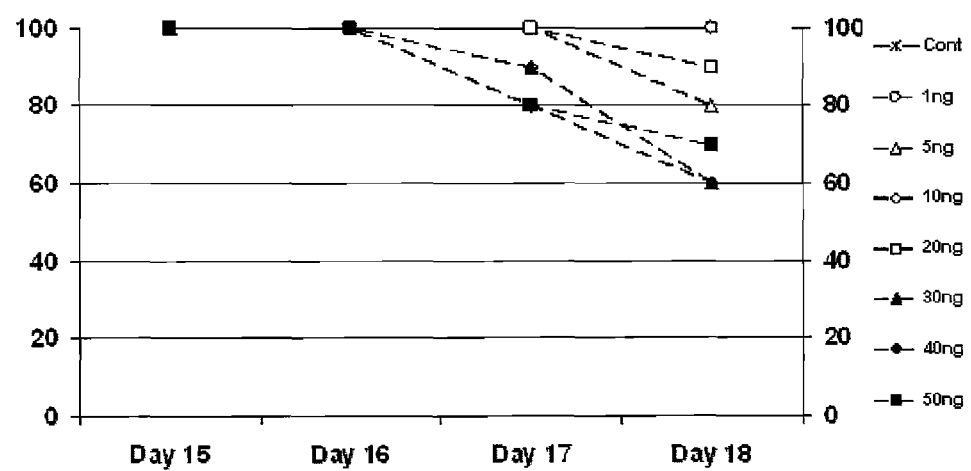

BoNT/A complex toxin, derived from type A Hall strain of *Clostridium botulinum*, was obtained from Metabiologics (Madison, Wis., USA) and was provided at 1 mg/ml total protein in 50 mM sodium citrate buffer, pH 5.5. The accompanying certificate states type A neurotoxin complex size (500 kDa) and toxicity ($3.2\times10^7$ $LD_{50}$/mg). The embryos were injected with BoNT/A diluted in approximately 0.85% saline solution (pH 7.0) at dosages of 0, 10, 50, 100, 150, 200, or 250 ng/embryo. The injection apparatus consisted of a 29 gauge (0.33 mm) half inch (12.7 mm) pen-needle (Autoshield™ 329300, Becton and Dickinson, Franklin Lakes, N.J., USA.) that was attached to a 1.0 ml tuberculin syringe. The spring-activated pen-needle guards provided complete needle coverage at all times other than when injecting the embryo through the eggshell. The syringe was loaded with multiple doses and each embryo was injected through the eggshell membrane into the neck with a volume of approximately 50 μL. Following injection, eggs were oriented vertically in eggflats, the eggflats were labeled for each injection code number, returned to the hatcher-incubator, and were no longer turned. At about 1, 2, and 3 days post-injection the viability of each embryo was reassessed by both candling and motion detection. Due to the high level of nonviability in Trial 1 ($\geq$93% at dosages of 50 ng BoNT/A and higher), lower dosages of the toxin were used in Trial 2 (0, 5, 10, 20, 30, 40, and 50 ng/embryo). Embryo viability data for Trial 1 is found in FIG. 1. For Trials 3 and 4 an additional group at 1 ng BoNT per embryo was included. Embryo viability data for Trial 2 is found in FIG. 2. Embryo viability data for Trial 3 is found in FIG. 3.

Figure 6A:
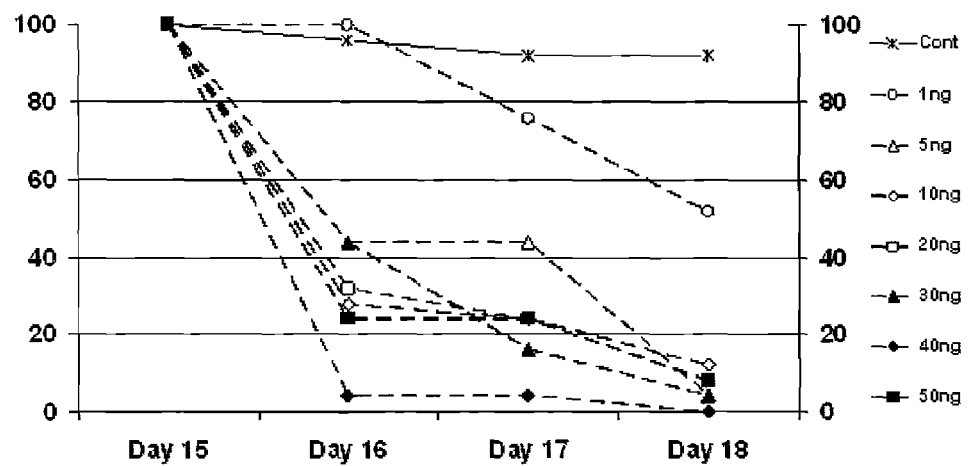
FIG. 6A shows the percentage of embryos alive without the antitoxin antibody.
Figure 6B:
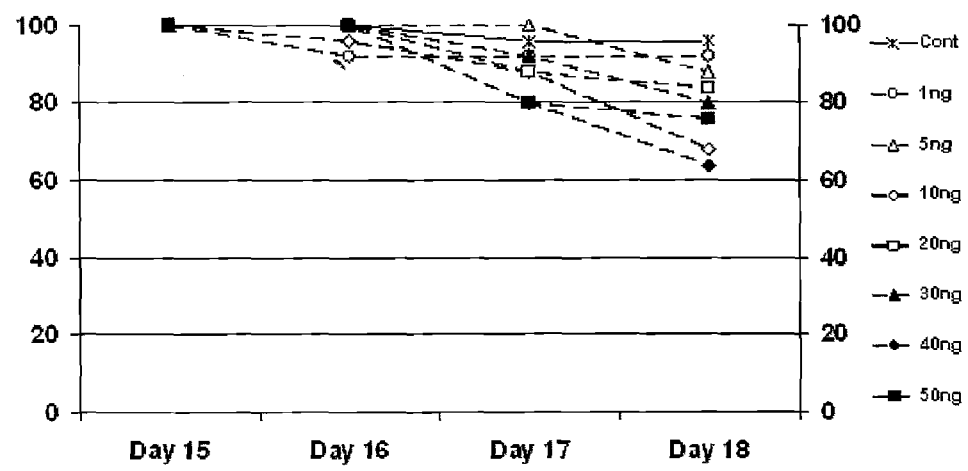
FIG. 6B shows the percentage of embryos alive with the antitoxin antibody.

Trails 4 and 5 included the addition of a duplicate set of BoNT dosages that had been mixed with BoNT/A antibody, (Metabiologics) to reveal botulinum toxin activity as the specific cause for nonviability in the injected embryos. Approximately ten μL of antibody was added to 1.1 ml of toxin (for 1 to 50 ng dosages) and swirled for 1 h prior to injection. In these two trials, there were 0 ng BoNT saline blanks both with and without antibody. The identity of the BoNT dosage groups and if they had contained antibody in Trials 4 or 5 were coded and remained unknown to the individual who injected the embryos and to the individual who determined daily embryo viability post-injection. Embryo viability data for Trial 4 is found in FIGS. 4 and 6. Embryo viability data for Trial 5 is found in FIGS. 5 and 6. For Trial 6 an additional dosage group of approximately 0.5 ng BoNT per embryo was included (0, 0.5, 1, 5, 10, 20, and 50 ng/embryo) and BoNT/A antibody was not utilized.

At the end of day 18 of incubation all unhatched eggs were opened, the embryos examined and classified by stage of embryonic development as modified for Japanese quail by observing the degree of yolk sac retraction (yolk sac not retracted stage 44, yolk sac ½-retracted stage 45, yolk sac ¾-retracted stage 45+, yolk sac entirely retracted stage 46−), and if the embryo had piped into the aircell or through the eggshell. This data is found in FIG. 7. In addition, any embryos that were determined to have developmental anomalies (brain hernia, beak or eye deformations) or positioned upside-down (away from the air cell) were recorded and then deleted from the total number of eggs set for the corresponding group (a total of 4/1,156 embryos). These embryos were excluded from the results because the abnormalities were not induced by the BoNT injection the previous day, and the abnormalities would have prevented the embryos progression to pipping and hatching.

Statistical analysis for BoNT dosages were analyzed by day post-injections (about 1, 2, and 3 days) using nonlinear regression plus linearization using transformation with the REG procedure of SAS software. Significance for viability of embryos at each dosage compared to the control or antibody compared to no antibody within a dose was analyzed using the Chi-square test procedure. For all analyses, significance was determined at $P<0.05$ level.

On about day 15 of incubation (the day of toxin injection), it was confirmed by observation that the quail embryos from this line and under the described egg storage and incubation conditions had not progressed to the developmental stage 45 as indicated by detecting that no embryos had pipped (n=50) into the aircell. The digital monitor was able to detect embryo pulse rate at about day 7 through 15 of incubation. As the embryo progressed to pipping into the aircell on day 16 of incubation, the digital monitor was no longer able to clearly display embryo pulse rate, due to the presence of ventilatory muscular movements that were depicted as rectangular waves on the display. Interpretation of the digital monitor wave patterns were confirmed by cutting a window through the eggshell into the aircell enabling observation of the embryo's orientation, stage of development, and musculoskeletal activity. It was noted that there were time periods when embryos that had pipped into the aircell did not continuously display consecutive maximum rectangular waves on the monitor's display. This was attributed to the embryo's ability to continue to utilize the chorioallantoic membrane for gas exchange and not depend entirely on pulmonary ventilation for gas exchange prior to pipping through the eggshell and hatching. The light candler was able to reveal the presence of the embryo's beak or head shadow movements within the aircell. However, accurate determination of embryo viability using the light candler was not possible for embryos that had not pipped into the aircell. Embryos that were not observed within the aircell by light candling and displayed flat-lines for 3 consecutive scans on the digital monitor were determined to be nonviable. This data is found in FIG. 8.

The results from the six trials were combined by dosage and are reported in Table 1. There were significant dosage linear regression responses at each day post-injection; about one day $P=0.0140$, about two days $P=0.0172$, and about three days $P=0.0391$. In Trial 1, from all embryos injected with BoNT/A at dosages from approximately 100 to approximately 250 ng only 1 of the 71 embryos completed hatching and only 3 were determined to be viable about 1 day post-injection. Embryo viability ranged from 5 to 7% (each representing a single embryo per dosage) at about 1 day post-injection. Therefore, the highest dosage used in subsequent trials was 50 ng/embryo. For embryos injected with approximately 20 to approximately 50 ng BoNT hatchability was extremely low from 9 to 14%. Embryos injected with approximately 5 and approximately 10 ng BoNT had very depressed hatchability at 26 and 24%, respectively. The embryos injected with approximately 1 ng BoNT had a moderately depressed hatchability of 54%, and those injected with approximately 0.5 ng BoNT had 50% hatchability and therefore this dosage appears to approximate the $LD_{50}$ for quail embryos. The 0 ng BoNT blank injected control embryos maintained a high hatchability of 96%. Although, embryos were prescreened for viability prior to injection, occasionally embryos possessed developmental abnormalities (1/1,156, missing eyes and brain hernia) or abnormal prehatch orientation (upside down 3/1,156) that are incompatible with pipping or hatching.

TABLE 1

Percentage and number of viable embryos detected the 1, 2, and 3 days post-injection

| Toxin dosage | Day of injection % (#) | One Day post-injection % (#) | Two Days post-injection % (#) | Three Days post-injection % (#) |
|---|---|---|---|---|
| 0 ng | 100 (#89) | 100 (#89) | 98 (#87) | 96 (#85) |
| 0.5 ng | 100 (#20) | 55 (#11)* | 55 (#11)* | 50 (#10)* |
| 1 ng | 100 (#76) | 67 (#51)* | 63 (#48)* | 54 (#41)* |
| 5 ng | 100 (#89) | 35 (#31)* | 35 (#31)* | 26 (#23)* |
| 10 ng | 100 (#94) | 30 (#28)* | 30 (#28)* | 24 (#23)* |
| 20 ng | 100 (#98) | 17 (#17)* | 13 (#13)* | 9 (#9)* |
| 30 ng | 100 (#77) | 26 (#20)* | 13 (#10)* | 10 (#8)* |
| 40 ng | 100 (#76) | 18 (#14)* | 21 (#16)* | 14 (#11)* |
| 50 ng | 100 (#69) | 22 (#15)* | 26 (#18)* | 13 (#9)* |
| 100 ng | 100 (#15) | 7 (#1)* | 7 (#1)* | 0 (#0)* |
| 150 ng | 100 (#19) | 5 (#1)* | 0 (#0)* | 0 (#0)* |
| 200 ng | 100 (#19) | 0 (#0)* | 0 (#0)* | 0 (#0)* |
| 250 ng | 100 (#18) | 6 (#1)* | 6 (#1)* | 6 (#1)* |

*Indicates that these dosages differ significantly from the control ($P < 0.01$) by chi square.
Transformation regressions and P values:
One Day post-injection: $y = 44.81 - 0.22 \log x$, $P = 0.0140$.
Two Days post-injection: $y = 42.82 - 0.22 \log x$, $P = 0.0172$.
Three Days post-injection: $y = 35.97 - 0.19 \log x$, $P = 0.0391$.

In trials 4 and 5 the mixing of serotype-A specific antibody prior to injection principally inactivated the BoNT as was evident by hatchabilities of approximately 64% to approximately 92% for toxin dosages from approximately 1 to approximately 50 ng (Table 2). Two days post-injection, those embryos injected with BoNT that was premixed with antibody maintained viability from approximately 80 to 100%, comparable to control embryos (injected with saline solution) at 96% viable. The addition of antibody to the 0 ng BoNT blank saline control did not impact embryos viability, which was 100%. About three days post-injection, the percentage point increase in viability for embryos injected with BoNT that was premixed with antibody ranged from about 38 percentage points (from 52 to 92%) for BoNT dosage of approximately 1 ng, to about 64 percentage points for BoNT dosage of approximately 5 ng (from approximately 24 to 88%). The percentage point increase in viability for embryos injected with BoNT that was premixed with antibody for BoNT dosages from approximately 10 to approximately 50 ng ranged from about 48 to 76 percentage points, respectively.

TABLE 2

Percentage and number of viable embryos on the 1, 2, and 3 days post-injection, without and with added antibody (Ab)

| Toxin dosage without or with antibody | Day of injection % (#) | One Day post-injection % (#) | Two Days post-injection % (#) | Three Days post-injection % (#) |
|---|---|---|---|---|
| 0 ng | 100 (#24) | 100 (#24) | 96 (#23) | 96 (#23) |
| 0 ng + Ab | 100 (#24) | 100 (#24) | 100 (#24) | 100 (#24) |
| 1 ng | 100 (#25) | 100 (#25) | 76 (#19) | 52 (#13) |
| 1 ng + Ab | 100 (#25) | 92 (#23) | 92 (#23)* | 92 (#23)† |
| 5 ng | 100 (#25) | 44 (#11) | 44 (#11) | 24 (#6) |
| 5 ng + Ab | 100 (#25) | 100 (#25)† | 100 (#25)† | 88 (#22)† |
| 10 ng | 100 (#25) | 28 (#7) | 24 (#6) | 20 (#5) |
| 10 ng + Ab | 100 (#25) | 96 (#24)† | 88 (#22)† | 68 (#17)† |
| 20 ng | 100 (#24) | 32 (#8) | 24 (#6) | 8 (#2) |
| 20 ng + Ab | 100 (#25) | 100 (#25)† | 88 (#22)† | 84 (#21)† |
| 30 ng | 100 (#25) | 44 (#11) | 16 (#4) | 12 (#3) |
| 30 ng + Ab | 100 (#25) | 100 (#25)† | 92 (#23)† | 80 (#20)† |
| 40 ng | 100 (#25) | 4 (#1) | 4 (#1) | 0 (#0) |
| 40 ng + Ab | 100 (#25) | 100 (#25)† | 80 (#20)† | 64 (#16)† |
| 50 ng | 100 (#25) | 24 (#6) | 24 (#6) | 8 (#2) |
| 50 ng + Ab | 100 (#25) | 100 (#25)† | 80 (#20)† | 76 (#19)† |

*Indicates significantly improved viability with the addition of antibody ($P < 0.05$).
†Indicates significantly improved viability with the addition of antibody ($P < 0.01$).

Figure 7:
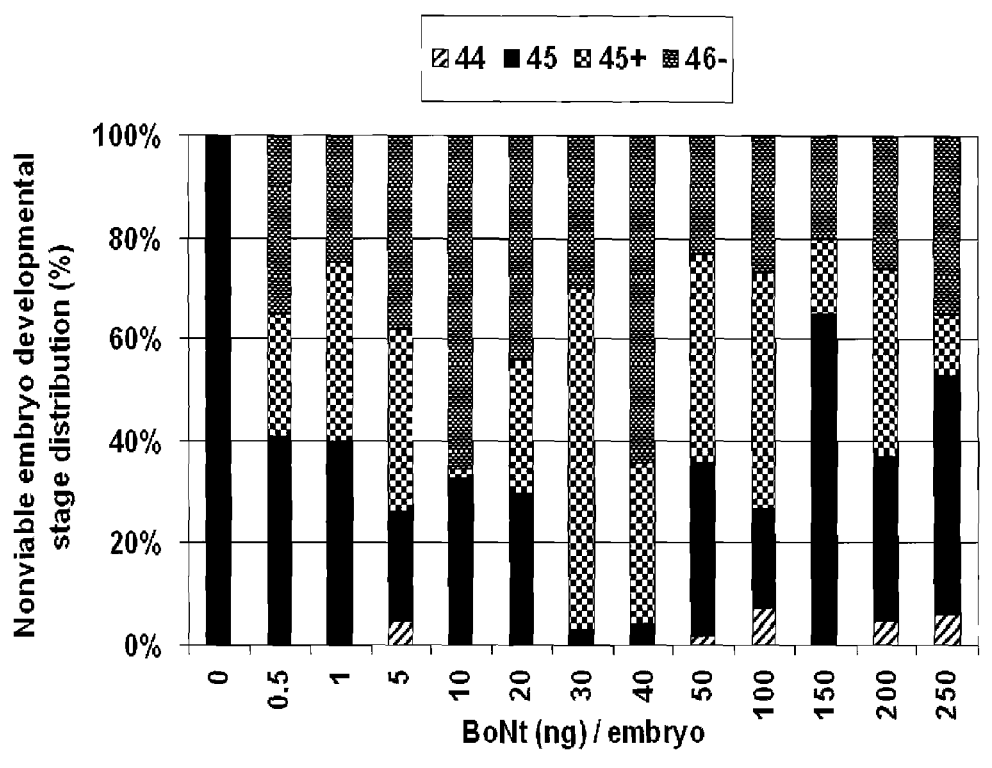

The injection of quail embryos with BoNT on about day 15 of incubation did not influence the embryo's ability to continue the progression of yolk sac retraction into the abdominal cavity. In FIG. 7, 100% of the control embryos (0 ng BoNT; n=4) that were determined to be nonviable had initiated yolk sac retraction and attained stage 45 of embryonic development. Nonviable embryos detected post-injection with BoNT dosages from approximately 0.5 to approximately 250 ng had also initiated yolk sac retraction with about 5 to 65% of the embryos at stage 45. Furthermore, about 45 to 95% of the BoNT injected nonviable embryos had yolk sac retraction that progressed beyond stage 45. Yolk sac retraction is accomplished by rhythmic contractions of the abdominal wall and the umbilical ring muscles[32] and does not appear to be influenced by BoNT injection at any dosage.

Figure 8:
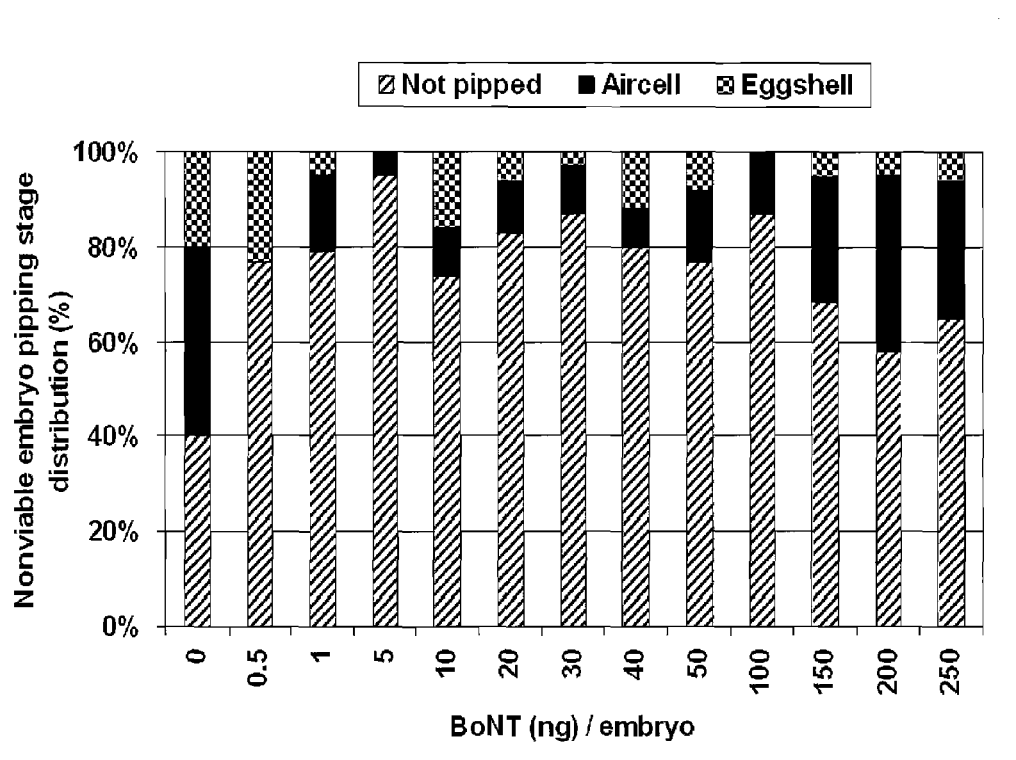

In contrast, injection of embryos in the neck with BoNT on about day 15 of incubation did prevent the developmental progression to aircell and eggshell pipping and the corresponding initiation of pulmonary ventilation, FIG. 8. About forty percent of the nonviable embryos in the control group had not progressed to pipping into the aircell, about 40% had pipped into the aircell, and about 20% had pipped through the eggshell. This contrasted markedly with the nonviable embryos injected with BoNT dosages from approximately 0.5 to approximately 250 ng with from about 58 to 78% of the embryos failing to progress to pipping into the aircell, from about 0 to 40% accomplished pipping into the aircell, and only from about 0 to 15% had pipped the eggshell.

EXAMPLE 2

Quail eggs were collected for about two days from the randombred control Line "C" of Japanese quail (*Coturnix japonica*) maintained at the University of Georgia (Darden & Marks 1988) for Experiment 1. For Experiment 2, quail eggs from the Louisiana High and Low plasma corticosterone response to brief mechanical immobilization lines and the corresponding Control line were transported to Athens from Louisiana State University (Satterlee and Johnson, 1988). Eggs were incubated at approximately 37.7 C and approximately 55% relative humidity and automatically turned through a 90° arc every hour. After about 14 days of incubation, embryo viability was assessed by both light candling and with Digital Egg Monitor (Avian Biotech International, Buddy V2). Eggs were randomly divided into groups of 10 viable embryos on eggflats and returned to the hatching incubator operating at approximately 37.7 C with the relative humidity raised to approximately 70%. The injection apparatus consisted of a 29 gauge (0.33 mm) half inch (12.7 mm) pen needle (Becton and Dickinson, Autoshield™ 329300) attached to a 1.0 mL tuberculin syringe. Experimental set up after injection was as described in Example 1 above.

Figure 9:
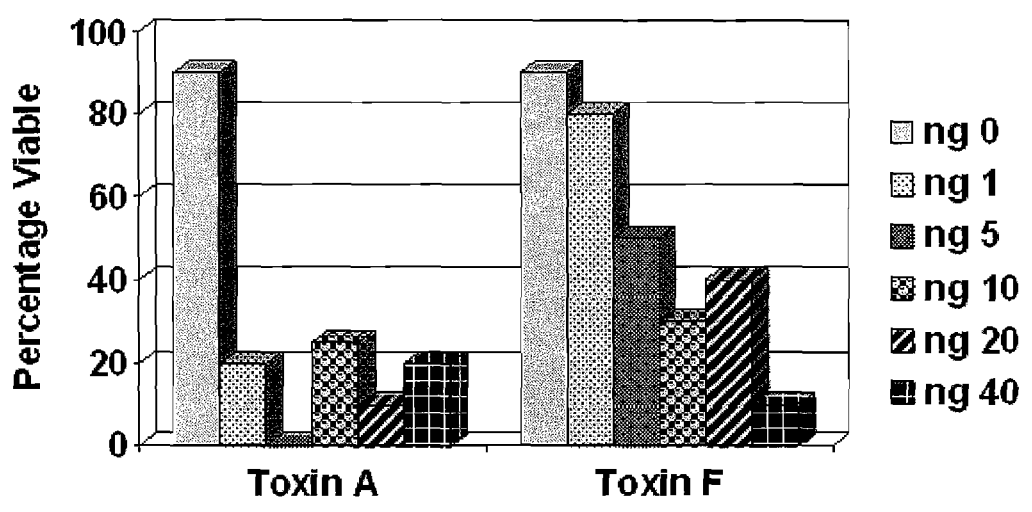

For UGA lines, embryos were injected with BoNT/A and F at approximately 0, 1, 5, 10, 20 and 40 ng, or were injected with BoNT/B and E at approximately 0, 10, 20, 40 and 50 ng. Toxins were suspended in gelatin (0.2%) 0.05 M phosphate buffer, pH 6.0. BoNT/B and E require trypsin activation at pH 6.0 for about 60 minutes at approximately 35-37 C prior to injection. Data is found in FIG. 9 and FIG. 10.

For the LSU quail lines, embryos were injected with BoNT/A and F at approximately 0, 1, 2.5, 5 and 10 ng. Embryos from the three lines (High, Low, and Control) were all injected from the same toxin dosage vial. Data is found in FIG. 11 and FIG. 12.

The identity of the treatment dosages were coded and remained unknown to the individual who injected the embryos and to the individual who determined daily embryo viability following injection. At the end of about day-18 (about 3 days postinjection) all unhatched eggs were opened and embryos examined. Embryos were classified by stage of embryonic development, the degree of yolk sac withdrawal, and if the embryo had piped into the aircell or through the eggshell. Any embryos that were determined to have developmental anomalies (brain hernia, beak or eye deformations) or positioned upside-down in the eggshell were recorded. These embryos were then deleted from the total number of eggs set when it was presumed that the abnormality would have prevented hatching.

Figure 10:
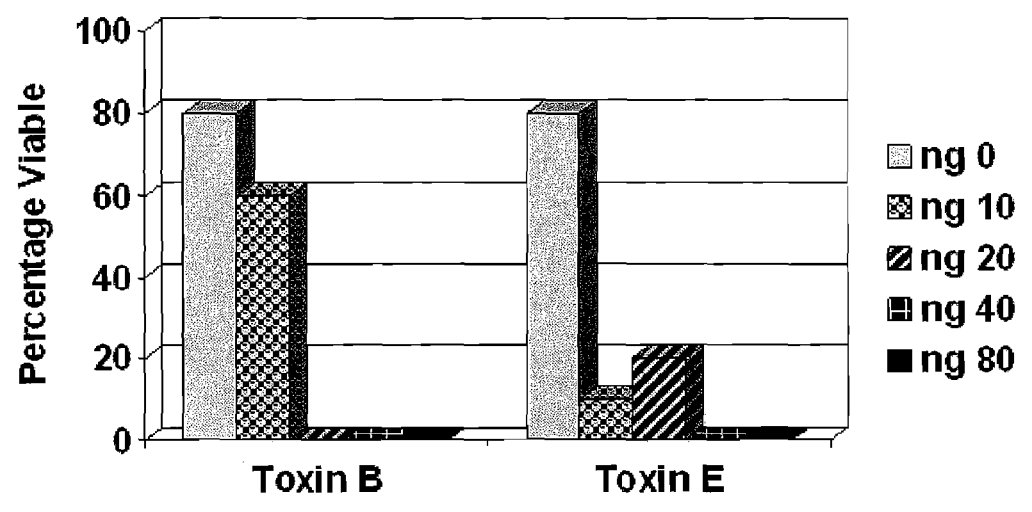
Figure 11:
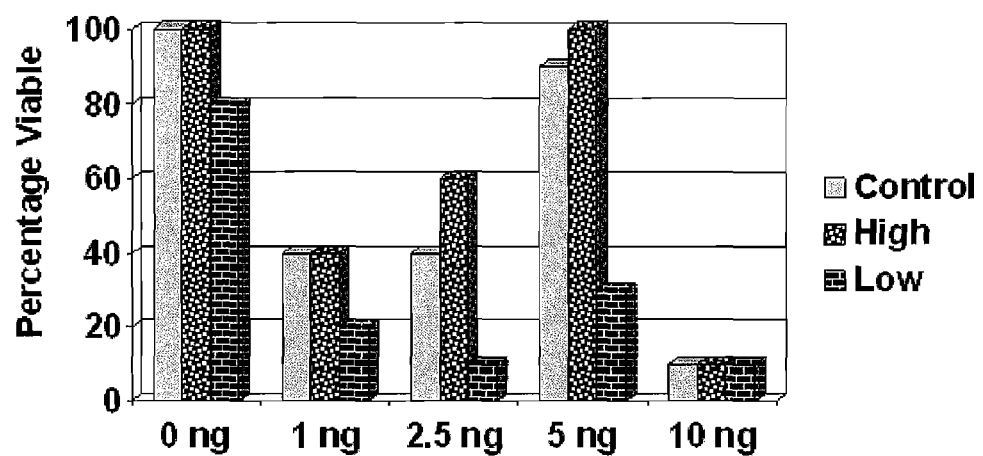
FIG. 11 shows embryo viability for control, high and low lines at 0-10 ng for BoNT/A.
Figure 12:
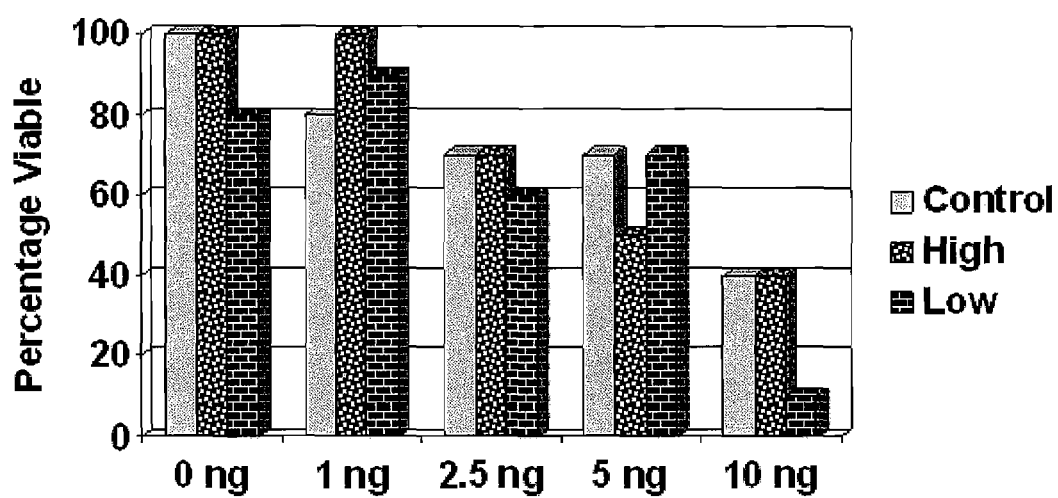
FIG. 12 shows embryo viability for control, high and low lines at 0-10 ng for BoNT/F.

The viability of UGA C-line embryos injected with the gelatin-phosphate buffer with 0 ng of toxin was approximately 90% at about 3 days post-injection, (FIG. 11). Embryos injected with BoNT/A at dosages from approximately 1, 5, 10, 20, to 40 ng had consistently low viability for all dosages at approximately 20, 0, 25, 10, and 20%, (FIG. 11). Those embryos injected with BoNT/F at dosages of approximately 1, 5, 10, 20, to 40 ng had progressively lower viability with increasing dosages from approximately 80, 50, 30, 40, to 10% viable, (FIG. 12). Embryos injected with the trypsin activation solution with 0 ng of toxin resulted in about 80% viable embryos indicating a slight depression in viability attributable to the trypsin, (FIG. 10). Embryos injected with trypsin activated BoNT/B at approximately 10, 20, 40, 80 ng had viability of approximately 60, 0, 0, and 0% and those injected with trypsin activated BoNT/E had viabilities of approximately 10, 20, 0, and 0%, (FIG. 10).

The LSU Low stress response line was about 50% more sensitive to BoNT/A and about 18% more sensitive for BoNT/F than the High stress response or the Control quail lines (which did not differ in viability), (FIGS. 11 and 12). For the BoNT/A injected embryos the High response quail line exceeded the Control line in viability when injected at approximately 2.5 ng (20%) and at approximately 5 ng (10%). For the BoNT/F injected embryos the High response quail line exceeded the Control line in viability by about 20% when injected at approximately 1 ng but was about 20% lower in viability when injected at approximately 5 ng.

The foregoing detailed description is for the purpose of illustration. Such detail is solely for that purpose and those skilled in the art can make variations therein without departing from the spirit and scope of the invention.

What is claimed is:

1. A method for detecting a botulinum toxin comprising:
   (a) puncturing an avian egg containing a viable embryo with a puncturing means to create two puncture holes in said egg wherein a first puncture hole is below the margin of said egg's air cell and a second puncture hole is above the center of said air cell,
   (b) injecting a sample suspected to contain a botulinum toxin into the neck of said viable embryo by inserting a needle through said first puncture hole and through the membrane of said egg, and
   (c) assessing viability of said embryo at days one, two and three post injection in order to determine if said toxin is present in said sample;
   wherein said assessing viability includes determining embryo movement and pulse rate of said embryo wherein no movement and pulse rate indicate the presence of a botulinum toxin.

2. The method of claim 1 wherein a high speed automated injection system is used to administer said sample suspected of containing a botulinum toxin.

3. The method of claim 1 wherein said method further comprises injecting the neck of at least one avian egg containing a viable embryo with a mixture containing at least one botulinum toxin serotype-specific antibody and a sample suspected of containing a botulinum toxin to confirm the presence of a botulinum toxin.

4. The method of claim 1 wherein said avian egg containing a viable avian embryo is selected from the group consisting of quail, chicken, turkey, duck, geese, pheasant, and ostrich.

* * * * *